(12) United States Patent
Richter et al.

(10) Patent No.: US 7,194,314 B1
(45) Date of Patent: Mar. 20, 2007

(54) COCHLEAR IMPLANT INCLUDING A MODIOLAR RETURN ELECTRODE

(75) Inventors: Claus-Peter Richter, Skokie, IL (US); Steven Ho, Evanston, IL (US)

(73) Assignee: Northwestern University, Evanston, IL (US)

(*) Notice: Subject to any disclaimer, the term of this patent is extended or adjusted under 35 U.S.C. 154(b) by 360 days.

(21) Appl. No.: 10/641,551

(22) Filed: Aug. 15, 2003

(51) Int. Cl.
*A61N 1/04* (2006.01)

(52) U.S. Cl. ............... 607/57; 607/55; 607/56; 607/136; 607/137; 600/25; 623/10

(58) Field of Classification Search ........... 607/55–57, 607/136–137, 2; 623/10; 600/25
See application file for complete search history.

(56) References Cited

U.S. PATENT DOCUMENTS

| | | | |
|---|---|---|---|
| 5,749,912 A * | 5/1998 | Zhang et al. ............... 607/57 |
| 6,157,861 A | 12/2000 | Faltys et al. |
| 6,163,729 A | 12/2000 | Kuzma |
| 6,249,704 B1 * | 6/2001 | Maltan et al. ............... 607/57 |
| 6,266,568 B1 * | 7/2001 | Mann et al. ............... 607/137 |
| 6,272,382 B1 | 8/2001 | Faltys et al. |
| 6,304,787 B1 | 10/2001 | Kuzma et al. |
| 6,308,101 B1 | 10/2001 | Faltys et al. |
| 6,321,125 B1 | 11/2001 | Kuzma |
| 6,358,281 B1 | 3/2002 | Berrang et al. |
| 6,374,143 B1 | 4/2002 | Berrang et al. |
| 6,397,110 B1 | 5/2002 | Kuzma |
| 6,415,185 B1 * | 7/2002 | Maltan ............... 607/57 |
| 6,421,569 B1 | 7/2002 | Treaba et al. |
| 6,496,734 B1 * | 12/2002 | Money ............... 607/56 |
| 6,889,094 B1 * | 5/2005 | Kuzma et al. ............... 607/137 |
| 2005/0033384 A1 * | 2/2005 | Sacha ............... 607/57 |

OTHER PUBLICATIONS

"The Cochlear Implant"; Retrieved from the internet: <URL: http://www.earspecialtygroup.com/esgimplant1.html; Feb. 19, 2003, pp. 1-3.
"Focusing Electrodes for Fine Details of Sound"; comparison chart; Clarion CII Bionic Ear System Features; prior to Feb. 19, 2003, pp. 7-8.
"The Med-EI combi 40+", Products Electrode Arrays; Retrieved from the Internet: <URL: http://www.medel.com/qs/languages/us/products/combi40+/combi40+.html; Feb. 19, 2003.

(Continued)

*Primary Examiner*—Robert Pezzuto
*Assistant Examiner*—Shevon Johnson
(74) *Attorney, Agent, or Firm*—Reinhart Boerner Van Deuren, S.C.

(57) ABSTRACT

A cochlear implant wherein the return path of the electrode array is located to increase current flow through the modiolus. The return electrode is placed at various locations outside the cochlea, and into the modiolus itself. In addition, the electrode array includes an inflatable membrane that is inflated to anchor the array in position in the cochlea with the electrode contacts pressed into contact with the modiolar wall and allowing the membrane to seal with the surrounding tissue of the cochlea, increasing the longitudinal resistance along the cochlear implant electrode, decreasing shunting of the injected current via scala tympani. In experiments that were conducted the current along the modiolus was determined to be, on average, 2.4 times larger with the return electrode in the modiolus than in an extracochlear location.

34 Claims, 10 Drawing Sheets

OTHER PUBLICATIONS

Lenarz, T., Lesinski-Schiedat, A., Weber, B.P., Frohne, C., Buchner, A., Battmer, R.D., Parker, J., and Von Wallenberg, E. "The Nucleus Double Array Cochlear Implant: a new concept in obliterated cochlea"; Laryngorhinootologie; 1999; 78(8):421-8 (with translation).

Richter, C-P. "Cochlear Electroanatomy: Impact on Protheses Design"; Slide show presentation, slides 1-25, presented at the Meeting of the Japanese Association of Otolaryngology, Oct. 4, 2002, Japan.

Badi, A.N. Hillman, T., Shelton, C. and Normann, R.A. "A Techique for Implantation of a 3-Dimensional Penetrating Electrode Array in the Modiolar Nerve of Cats and Humans"; Arch. Otolaryngol. Head Neck Surg. 128(9):1019025 (2002).

Bigelow, D.C., Kay, D.J., Rafter, K.O., Montes, M., Knox, G.W. and Yousem, D.C. "Facial Stimulation from Cochlear Implants"; Am. J. Otol. 19:163-9 (1998).

Black, R.C., Clark, G.M. and Patrick, J.F. "Current Distribution Measurements within the Human Cochlea"; IEEE Trans. Biomed. Eng. 28:721-725(1981).

Busby, P.A. Tong, Y.C. and Clark, G.M. "Electrode Position, Repetition Rate, and Speech Perception by Early- and Late-Deafened Cochlear Implant Patients"; J. Acoust. Soc. Am. 93(2):1058-67 (1993).

Clark, G.M. "Cochlear Implants in the Third Millennium"; Am. J. Otol. 20(1):4-8 (1999).

Clark, G.M., Shepherd, R.K., Patrick, J.F., Black, R.C. and Tong, Y.C. "Design and Fabrication of the Banded Electrode Array"; Ann. N.Y. Acad. Sci. 405:191-201 (1993).

Cords, S.M., Reuter, G., Issing, P.R., Sommer, A., Kuzma, J. and Lenarz, T. "A Silastic Positioner for a Modiolus-Hugging Position of Intracochlear Electrodes: Electrophysiologic Effects"; Am. K. Otol. 21(2):212-7 (200).

Faltys, M., Segel, P., Gord, J., Voelkel, A., Kessler, D. and Finley, C. "Electric Field Imaging Methodology"; Conference on Implantable Auditory Prosthesis, Pacific Grove, CA (2001.

Fayad, J.N., Luxford, W. and Linthicum, F.H. "The Clarion Electrode Positioner: Temporal Bone Studies"; Am. J. Otol. 21(s):226-9 (2000).

Friesen, L.M., Shannon, R.V. and Slattery, W.H. "Effects of Electrode Location on Speech Recognition with the Nucleus-22 Cochlear Implant"; J. Am. Acad, Audiol. 11(8):418-28 (2000).

Ho, S. and Richter, C-P. "Electrode Placement Affects Current Paths in the Implanted Cochlea"; Meeting of the Association of Research of Otolaryngology. Feb. 22-27 (2003).

Hochmair, E.S. "System Optimization for Improved Accuracy in Transcutaneous Signal and Power Transmission"; IEEE Tans. Biomed. Eng. 31(2):177-86 (1984).

Ifukube, T. and White, R.L. "A Speech Processor with Lateral Inhibition for an Eight Channel Cochlear Implant and its Evaluation"; IEEE Trans. Biomed. Eng. 34(11):876-82 (1987).

Jolly, C.N., Spelman, F.A. and Clopton, B.M. "Quadrupolar Stimulation for Cochlear Prothesis: Modeling and Experimental Data"; IEEE Trans. Biomed. Eng. 43(8):857-65 (1996).

Kelsall, D.C., Shallop, J.K., Brammeier, T.G. and Prenger, E.C. "Facial Nerve Stimulation after Nucleus 22-Channel Cochlear Implantation"; Am. J. Otol. 18(3):336-41 (1997).

Kral, A., Hartman, R., Mortazavi, D. and Clinke, R. "Spatial Resolution of Cochlear Implants: The Electrical Field and Excitation of Auditory Afferents"; Hearing Research 121(1-2):11-28 (1998).

Liang, D.H., Lusted, H.S. and White, R.L. "The Nerve-Electrode Interface of the Cochlear Implant: Current Spread"; IEEE Trans. Biomed. Eng. 46(1):35-43 (1999).

Loeb, G.E., White, M.W. and Jenkins, W.M. "Biophysical Considerations in Electrical Stimulation of the Auditory Nervous System"; Ann. N.Y. Acad. Sci. 405(4):123-36 (1983).

Luxford, W.M. "Surgery for Cochlear Implantation"; In Brackmann, Shelton, Arriaga, editors. Otologic Surgery. 425-436 (1994).

Rebscher, S.J., Heilmann, M., Bruszewski, W., Talbot, N.H., Snyder, R.L. and Merzenich, M.M. "Strategies to Improve Electrode Positioning and Safety in Cochlear Implants"; IEEE Trans. Biomed. Eng. 46:340-352 (1999).

Richter, C-P, Koch, D.B. and Rao, R. "The Hemicochlea; A Tool to Evaluate Potential Distributions in the Electrically Stimulated Cochlea"; Conference on Implantable Auditory Prostheses, Pacific Grove, CA (2001).

Rodenhiser, K.L. and Spelman, F.A. "A Method for Determining the Driving Currents for Focused Stimulation in the Cochlea"; IEEE Trans. Biomed. Eng. 42(4):337-42 (1995).

Roland, J.T., Fishman, A.J., Alexiades, G. and Cohen, N.L. "Eloctrode to Modiolus Proximity: A Fluoroscopic and Histologic Analysis"; Am. J. Otol. 21(2):218-25 (2000).

Rousche, P.J. and Normann, R.A. "Chronic Intracortical Miscrostimulation (ICMS) of Cat Sensory Cortex Using the Utah Intracortical Electrode Array"; IEEE Trans. Rehab. Eng. 7(1):56-68 (1999).

Rubenstein, J.T., Spelman, F.A., Soma, M. and Suesserman, M.F. "Current Density Profiles of Surface Mounted and Recessed Electrodes for Neural Protheses"; Trans. Biomed. Eng. 34(11):864-75 (1987).

Simmons, F.B. "Percepts from Modiolar (Eighth Nerve) Stimulation"; Ann. N.Y. Acad. Sci. 405:259-63 (1983).

Spelman, F.A. Pfingst, B.E., Clopton, B.M., Jolly, C.N. and Rodenhiser, K.L. "Effects of Electrical Current Configuration on Potential Fields in the Electrically Stimulated Cochlea: Field Models and Measurements"; Ann. Otol. Rhinol. Laryngol. Suppl. 166:131-6 (1995).

Suesserman, M.F. and Spelman, F.A. "Quantitative In Vivo Measurements of Inner Ear Tissue Resistivities: I. In Vivo Characterization"; IEEE Trans. Biomed. Eng. 40(10):1032-47 (1993).

Suesserman, M.F., Spelman , F.A. and Rubinstein, J.T. "In Vitro Measurement and Characterization of Current Density Profiles Produced by Nonrecessed, Simple Recessed, and Radially Varying Recessed Stimulating Electrodes"; IEEE Trans. Biomed. Eng. 38(5):401-8 (1991).

Townshend, B. and White, R.L. "Reduction of Electrical Interaction in Auditory Prosthesis"; IEEE Trans. Biomed. Eng. 34(11):891-897 (1987).

Vivion, M.C., Merzenich, M.M., White, M., Leake-Jones, P.A. and Silverman, M. "Electrode Position and Excitation Patterns for a Model Cochlear Prosthesis"; Ann. Otol. Rhinol. Laryngol. Suppl. 90(2 Pt 3):19-20 (1981).

Zappia. J.J., Hetke, J.F., Altschuler, R.A. and Niparko, J.K. "Evaluation of A Silicon-Substrate Modiolar Eighth Nerve Implant in a Guinea Pig"; Ololaryngol. Head Neck Surg. 103(4):575-82 (1990).

Zierhofer, C.M., Hochmair, I.J. and Hochmair, E.S. "The Advanced Combi 40+ Cochlear Implant"; Am. J. Otol. 18(6 Suppl):S37-8 (1997).

* cited by examiner

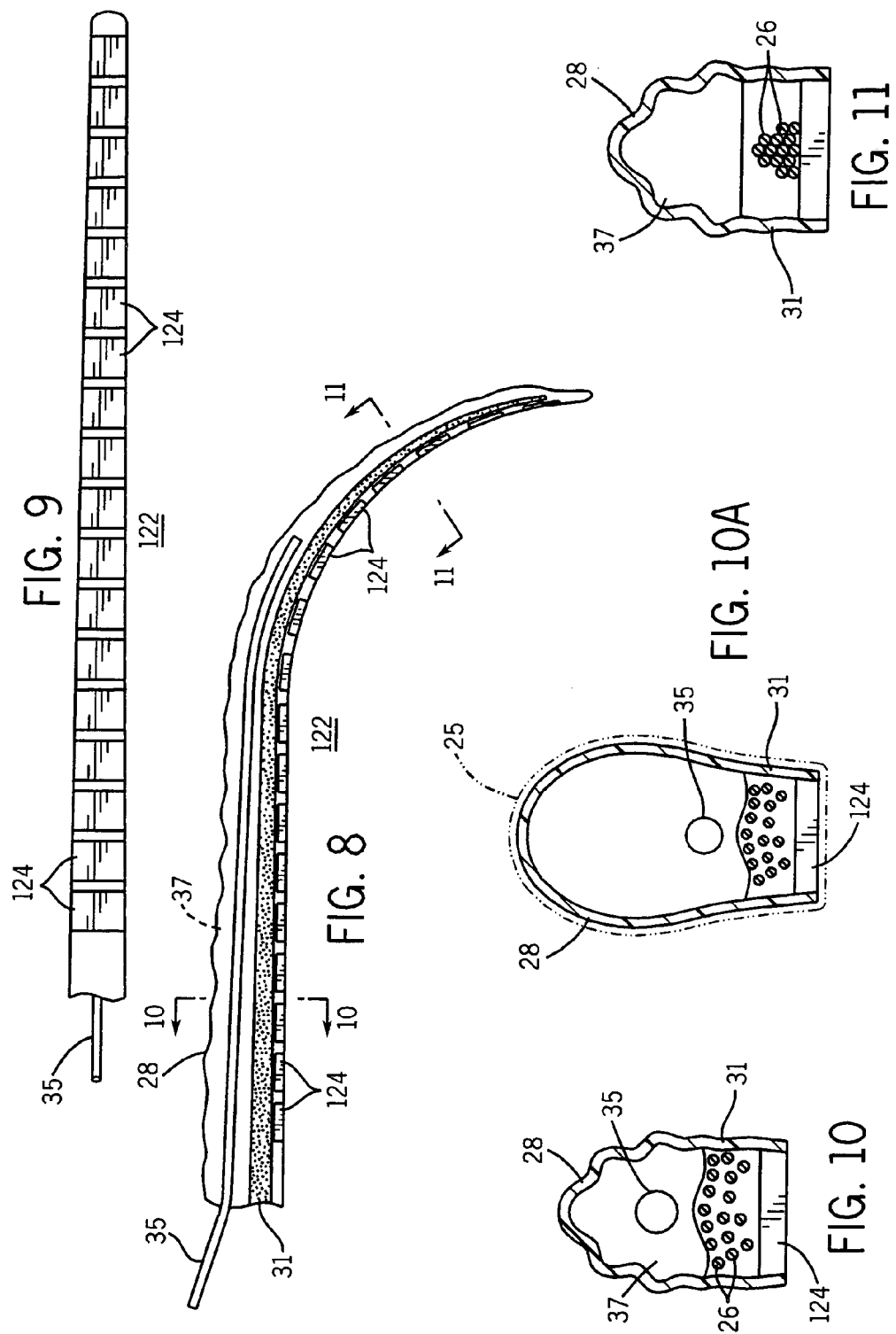

COCHLEAR IMPLANT INCLUDING A MODIOLAR RETURN ELECTRODE

BACKGROUND OF THE INVENTION

Field of the Invention

The present invention relates generally to cochlear implants used to electrically stimulate the auditory nerves, and more particularly to the design and positioning of an electrode array and a return electrode for a cochlear implant.

Cochlear implants have become an accepted and successful treatment for severe-to-profound deafness. However, cochlear implants require a large amount of power in order to provide effective stimulation. Contemporary devices send sound information processed by an external speech processor across the skin to an implanted receiver. This transmission consumes a large fraction of the power used by the speech processor and constitutes a major power loss in a cochlear implant. Another significant loss of power occurs in the cochlea at the electrode tissue interface, because the current is shunted away from the target structures in the modiolus [Black et al., 1981; Rubinstein et al., 1987; Suesserman et al., 1991; Suesserman, 1992; Suesserman and Spelman, 1993]. For any future fully implantable systems to be practical, the issue of power consumption must be addressed.

Recent efforts have been directed at finding strategies that will reduce power consumption without affecting the implant's performance. One strategy proposed has been to position the electrode array closer to the modiolus [Rebscher et al., 1999; Lenarz et al., 1999; Roland et al., 2000; Fayad et al., 2000; Cords et al., 2000; Friesen et al., 2000; Richter et al., 2001]. It is assumed that minimizing the physical distance between the current source and the target reduces the current necessary to stimulate surviving nerve fibers. Furthermore, lower currents minimize interactions between neighboring stimulating electrodes, and lessen the risk of damage due to current application. To achieve similar results, other strategies focus on refining the electrode designs, such as multipolar stimulation paradigms and electrode configurations [Vivion et al., 1981; Clark et al., 1983; Loeb et al., 1983; Hochmair, 1984; Rubinstein et al., 1987; Ifukube and White, 1987; Townshend and White, 1987; Busby et al., 1993; Rodenhiser and Spelman, 1995; Zierhofer et al., 1997; Clark, 1999; Liang et al., 1999].

The concept of implantation of stimulating electrodes into the modiolus has been proposed. However, technology was not adequate at that time to allow clinical applications [Simmons, 1983; Zappia et al., 1990]. Simmons and Zappia, both placed the stimulating electrode into the modiolus. The stimulating electrode has many contacts and is in general large in dimension. Spatial selectivity is achieved by the different contacts in the modiolus. Modiolar implants have been successfully inserted and proven to be safe in the short term follow-up as reported by Zappia and Badi [Zappia et al., 1990].

REFERENCES

The foregoing background information, together with other aspects of the prior art, including those teachings useful in light of the present invention, are disclosed more fully and better understood in light of the following references, each of which is incorporated herein in its entirety.

1. Badi, A, Hillman, T, Shelton, C, and Normann, R: A technique for implantation of a 3-dimensional penetrating electrode array in the modiolar nerve of cats and humans. Arch Otolaryngol Head Neck Surg. 2002;128(9):1019–25.
2. Bigelow, D C, Kay, D J, Rafter, K O, Montes, M, Knox, G W, and Yousem, D M: Facial Nerve stimulation from cochlear implants. Am. J. Otol. 1998;19:163–9.
3. Black, R C, Clark, G M, and Patrick, J F: Current distribution measurements within the human cochlea. IEEE Trans Biomed Eng. 1981;28:721–724.
4. Busby, P A, Tong, Y C, and Clark, G M: Electrode position, repetition rate, and speech perception by early- and late-deafened cochlear implant patients. J. Acoust. Soc. Am. 1993;93(2):1058–67.
5. Clark, G M: Cochlear implants in the Third Millennium. Am. J. Otol. 1999;20(1):4–8.
6. Clark, G M, Shepherd, R K, Patrick, J F, Black, R C, and Tong, Y C: Design and fabrication of the banded electrode array. Ann N. Y. Acad. Sci. 1983;405:191–201.
7. Cords, S M, Reuter, G, Issing, P R, Sommer, A, Kuzma, J, and Lenarz, T: A silastic positioner for a modiolus-hugging position of intracochlear electrodes: electrophysiologic effects. Am. J. Otol. 2000;21(2):212–7.
8. Fayad, J N, Luxford, W, and Linthicum, F H: The Clarion electrode positioner: temporal bone studies. Am. J. Otol. 2000;21(2):226–9.
9. Friesen, L M, Shannon, R V, and Slattery, W H 3rd: Effects of electrode location on speech recognition with the Nucleus-22 cochlear implant. J. Am. Acad. Audiol. 2000;11(8):418–28.
10. Hochmair, E S: System optimization for improved accuracy in transcutaneous signal and power transmission. IEEE Trans. Biomed. Eng. 1984;31(2):177–86.
11. Ifukube, T and White, R L: A speech processor with lateral inhibition for an eight channel cochlear implant and its evaluation. IEEE Trans. Biomed. Eng. 1987;34(11):876–82.
12. Kelsall, D C, Shallop, J K, Brammeier, T G, and Prenger, E C: Facial nerve stimulation after Nucleus 22-channel cochlear implantation. Am. J. Otol. 1997;18(3):336–41.
13. Lenarz, T, Lesinski-Schiedat, A, Weber, B P, Frohne, C, Buchner, A, Battmer, R D, Parker, J, and von Wallenberg, E: [The Nucleus Double Array Cochlear Implant: a new concept in obliterated cochlea]. Laryngorhinootologie. 1999;78(8):421–8.
14. Liang, D H, Lusted, H S, and White, R L: The nerve-electrode interface of the cochlear implant: current spread. IEEE Trans. Biomed. Eng. 1999;46(1):35–43.
15. Loeb, G E, White, M W, and Jenkins, W M: Biophysical considerations in electrical stimulation of the auditory nervous system. Ann. N. Y. Acad. Sci. 1983;405(4):123–36.
16. Luxford W M: Surgery for cochlear implantation. In Brackmann, Shelton, Arriaga, editors. Otologic Surgery. 1994; 425–436.
17. Rebscher, R J, Heilman, M, Bruszewski, W, Talbot, N H, Snyder, R L, and Merzenich, M M: Strategies to improve electrode positioning and safety in cochlear implants. IEEE Trans. Biomed. Eng. 1999;46:340–352.
18. Richter, C P, Koch, D B, and Rao, R: The hemicochlea: A tool to evaluate potential distributions in the electrically stimulated cochlea. CIAP. 2001.
19. Rodenhiser, K L and Spelman, F A: A method for determining the driving currents for focused stimulation in the cochlea. IEEE Trans. Biomed. Eng. 1995;42(4):337–42.

20. Roland, J T Jr, Fishman, A J, Alexiades, G, and Cohen, N L: Electrode to modiolus proximity: a fluoroscopic and histologic analysis. Am. J. Otol. 2000;21(2):218–25.
21. Rubinstein, J T, Spelman, F A, Soma, M, and Suesserman, M F: Current density profiles of surface mounted and recessed electrodes for neural prostheses. IEEE Trans. Biomed. Eng. 1987;34(11):864–75.
22. Simmons, B F: Percepts from modiolar (eight nerve) stimulation. Ann. N. Y. Acad. Sci. 1983;405:259–63.
23. Suesserman, M F: Noninvasive microelectrode measurement technique for performing quantitative, in vivo measurements of inner ear tissue impedances. 1992. University of Washington.
24. Suesserman, M F and Spelman, F A: Quantitative in vivo measurements of inner ear tissue resistivities: I. In vitro characterization. IEEE Trans. Biomed. Eng. 1993;40(10): 1032–47.
25. Suesserman, M F, Spelman, F A, and Rubinstein, J T: In vitro measurement and characterization of current density profiles produced by non-recessed, simple recessed, and radially varying recessed stimulating electrodes. IEEE Trans. Biomed. Eng. 1991;38(5):401–8.
26. Townshend, B and White, R L: Reduction of electrical interaction in auditory prostheses. IEEE. 1987;34(11): 891–897.
27. Vivion, M C, Merzenich, M M, Leake-Jones, P A, White, M, and Silverman, M: Electrode position and excitation patterns for a model cochlear prosthesis. Ann. Otol. Rhinol. Laryngol. Suppl. 1981;90(2 Pt 3):19–20.
28. Zappia, J J, Hetke, J F, Altschuler, R A, and Nipariko, J K: Evaluation of a silicon-substrate modiolar eight nerve implant in a guinea pig. Otolaryngol Head Neck Surg. 1990;103(4):575–82.
29. Zierhofer, C M, Hochmair, I J, and Hochmair, E S: The advanced Combi 40+ cochlear implant. Am. J. Otol. 1997;18(6 Suppl):S37–8.

SUMMARY OF THE INVENTION

The disadvantages and limitations of the background art discussed above are overcome by the present invention. With this invention, there is provided a method and apparatus for reducing current requirements, that is, to increase the current flow through the modiolus by altering the return electrode's placement.

In accordance with the invention, there is provided a method of implanting a cochlear implant in scala tympani of a human cochlea, the scala tympani including a modiolar wall. The method comprises the steps of providing a stimulating electrode array including a plurality of contacts, a plurality of conductors electrically connected to the contacts, an insulating member containing the conductors, the insulating member including an expandable portion; expanding the expandable portion to substantially fill the scala tympani and to urge the contacts into close proximity with neurons in Rosenthal's canal; and locating a return electrode into the modiolus.

Further in accordance with the invention, there is provided a method of locating a return electrode of a cochlear implant in scala tympani of a human cochlea. The method comprises the steps of providing an access opening to the scala tympani; providing an opening through the modiolar wall to expose tissue; inserting the return electrode into the opening in the modiolar wall; positioning the return electrode within the opening in the modiolar wall; and securing the electrode to the modiolar wall.

In contrast to the previous attempts, the present invention places a single return electrode into or at least close to the inner lumen of the modiolus. It has to be taken into account that a modiolar return electrode might act by itself as a stimulating electrode, because it is close to excitable tissue, the auditory nerve leaving the modiolus. Nonspecific stimulation of the nerve trunk would result. If nonspecific stimulation of the nerve trunk should occur, this problem can be overcome by three measures: (1) by retracting of the electrode into the hole drilled into the modiolus (2) by reducing the current density through increasing the physical area of the electrode, and (3) by using pseudo-monopolar stimuli so that only scala tympani electrodes act as active or stimulating electrodes. In addition to the return electrode, a cochlear implant array is inserted into scala tympani. Thus, spatial selectivity is obtained from the cochlear implant array, which can be the electrode array provided by the present invention or a conventional array, in scala tympani, while the return electrode in the modiolus provides a significant reduction in power consumption to achieve similar currents through the modiolus as achieved in contemporary cochlear implants.

The invention further provides a return electrode for a cochlear implant that is locatable in scala tympani of a human cochlea. The return electrode includes a body adapted for insertion into the opening in the modiolar wall, the body having a bore therethrough and an electrode including a conductor having a contact at one end, the conductor extending through the bore. The body defines a retaining mechanism for securing the body to the modiolar wall. In one embodiment, the body has a threaded outer surface defining the retaining mechanism and the body is screwed into the opening in the modiolar wall. In another embodiment, the body includes first and second humps spaced apart from one another, defining the retaining mechanism.

Further in accordance with the invention, there is provided a cochlear implant adapted to be implanted in scala tympani of a human cochlea. The cochlear implant includes a stimulating electrode array including a plurality of contacts, a plurality of conductors electrically connected to the contacts, an insulating member containing the conductors, the insulating member including an expandable portion adapted to be expanded to fill the scala tympani; and a return electrode adapted for mounting within the cochlea with at least a portion of the electrode extending into the modiolar wall, the return electrode extending within the stimulating electrode array.

In addition, the present invention provides a simplified model of the cochlea for demonstrating that the current along the nerve fibers in the modiolus can be increased approximately twofold by placing the return electrode into the modiolus. This corresponds to an approximate 4 fold decrease in power loss. Theoretical estimates are verified in human cadaver cochleae, which reveal a similar increase in modiolar current when the return electrode is placed in the modiolus rather than at extracochlear locations.

DESCRIPTION OF THE DRAWINGS

These and other advantages of the present invention are best understood with reference to the drawings, in which:

FIG. 8 illustrates a second embodiment of an electrode array in accordance with the invention;

FIG. 9 is a plan view of the electrode array of FIG. 8 and showing the arrangement of electrode contacts of the electrode array;

FIG. 10 is a section view taken along the line 10—10 of FIG. 8;

FIG. 10A is a section view similar to that of FIG. 10 and illustrating the inflatable membrane shown inflated into engagement with the scala tympani shown in phantom;

FIG. 11 is a section view taken along the line 11—11 of FIG. 8;

DETAILED DESCRIPTION OF THE PREFERRED EMBODIMENT

Figure 1:
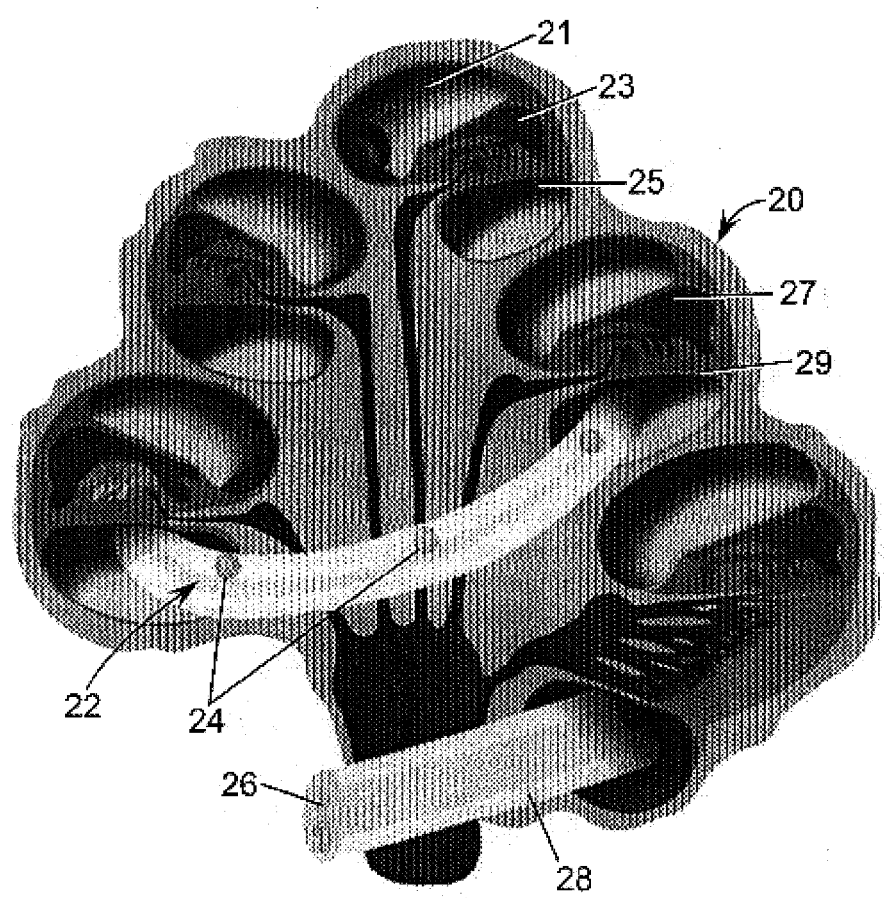
FIG. 1 is a cross section view of a cochlea having implanted therein an electrode array in accordance with the present invention.

Referring to FIG. 1, there is shown a cross section view of a cochlea 20 in which an electrode array 22 has been implanted. Portions of the cochlea 20 are identified in FIG. 1, including the scala vestibuli 21, the scala media 23, the scala tympani 25, Reisner's membrane 27 and the basilar membrane 29. The electrode array 22 includes electrode contacts 24, contact wires 26 and an inflatable body or membrane 28. The inflatable membrane 28 can be of rubber or a similar material. The electrode array 22 is positioned in cochlea with the electrode contacts 24 of the electrode array 22 facing the wall of the modiolus. In one embodiment, the electrode array 22 includes spherical electrode contacts 24 soldered to platinum-iridium wires 26. The electrode contacts 24 and the wires 26 are embedded in a silastic carrier that can be similar to silastic carrier 31 (FIG. 8) that is formed around the electrode contacts 24 and the wires 26. The inflatable membrane 28 and the silastic carrier of the electrode array 22 are kept as small as possible to allow easy insertion of the electrode array 22 into the cochlea with the electrodes 24 facing the modiolar wall of the cochlea. When the electrode array is in position in the cochlea, the inflatable membrane is inflated, such as by filling the membrane 28 with silicone, to anchor the electrode array 22 in position in the cochlea with the electrode contacts pressed into contact with the modiolar wall and allowing the inflatable membrane 28 to seal with the surrounding tissue of the cochlea, increasing the longitudinal resistance. While in a preferred embodiment the electrode array 22 includes an inflatable membrane 28, a conventional electrode can be used.

Figure 2:
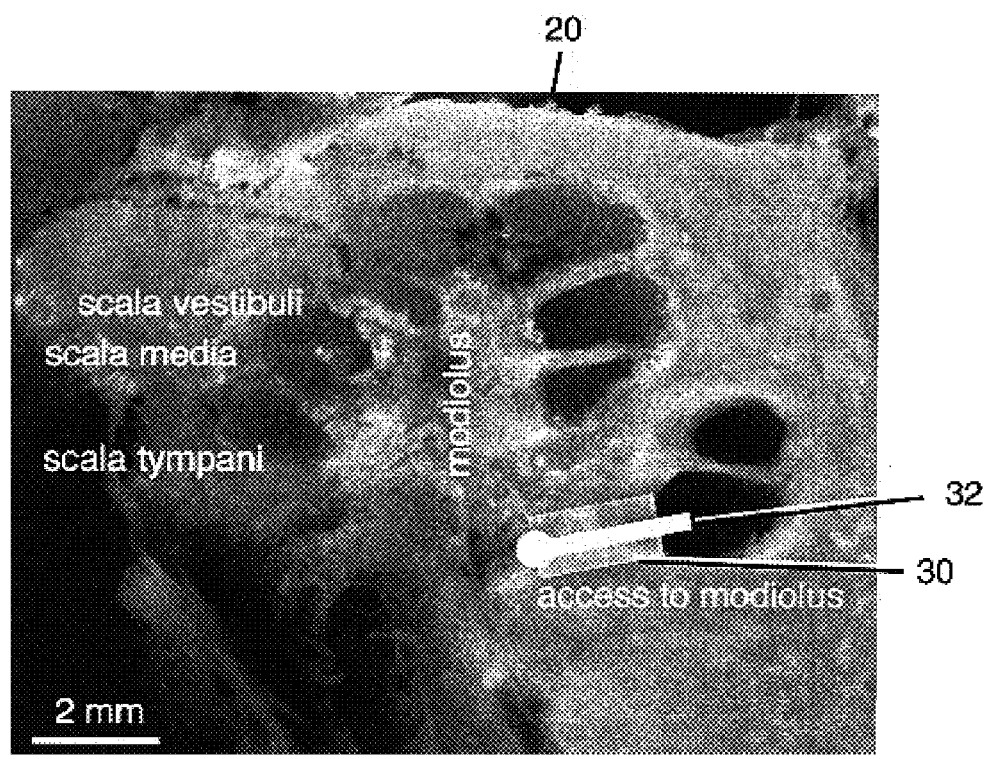
FIG. 2 is an enlarged view of a portion of a human cochlea, sliced along its mid modiolar plane and showing the cochlear implant electrode array generally inserted into scala tympani and a return electrode inserted into the modiolus via an opening drilled into the cochlear wall indicated by the white shaded area in accordance with the invention.

Referring also to FIG. 2, which is a cross sectional view of the cochlea 20 shown in FIG. 1, the electrode array 22 shown in FIG. 1 further includes a return electrode 32, shown in FIG. 2, which is located in the modiolus in accordance with the present invention. FIG. 2 is an enlarged view of a portion of a human cochlea, sliced along its mid modiolar plane and showing the cochlear implant electrode array generally inserted into scala tympani and a return electrode inserted into the modiolus via an opening drilled into the cochlear wall indicated by the white shaded area 30. As will be shown, locating the return electrode 32 in the modiolus rather than outside the modiolus, and under identical stimulation conditions, can increase modiolar current by a factor of up to about 2.7.

One of the advantages of the electrode array 22 over known electrode arrays is that electrode array 22 significantly reduces power loss due to shunting currents along scala tympani. The electrode array 22 also reduces current values that result in reduced risk of tissue damage. In addition, the electrode array 22 is characterized by increased spatial selectivity. The contact wires 26 of the electrode array 22 and the return electrode 32 can be connected to any known speech processor (not shown) for receiving stimulating signals.

Figure 3:
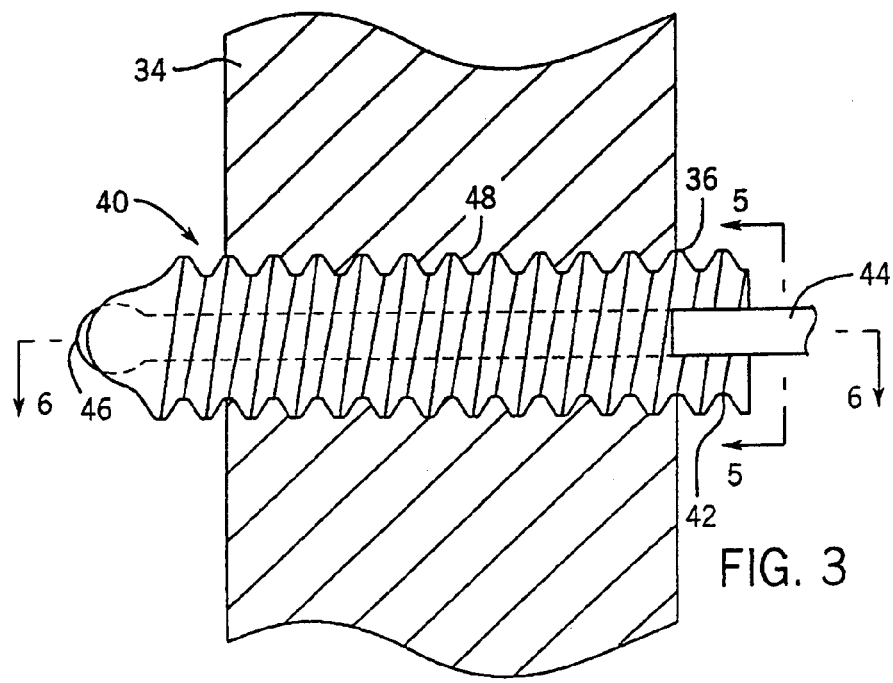
FIG. 3 illustrates one embodiment of a return electrode in accordance with the invention, shown mounted in the modiolus.

FIG. 3 is a simplified representation of one embodiment of a return electrode 40 adapted to be mounted in the modiolus 34 in accordance with the invention. The return electrode 40 includes a body portion 42 through which extends an electrode wire 44 having a tip 46 formed at its distal end. The outer surface 48 of the body portion 42 of the return electrode 40 is threaded to allow the return electrode 40 to be screwed into a hole 36 formed in the bone of the modiolus 34 for anchoring the return electrode to the modiolus.

Figure 4:
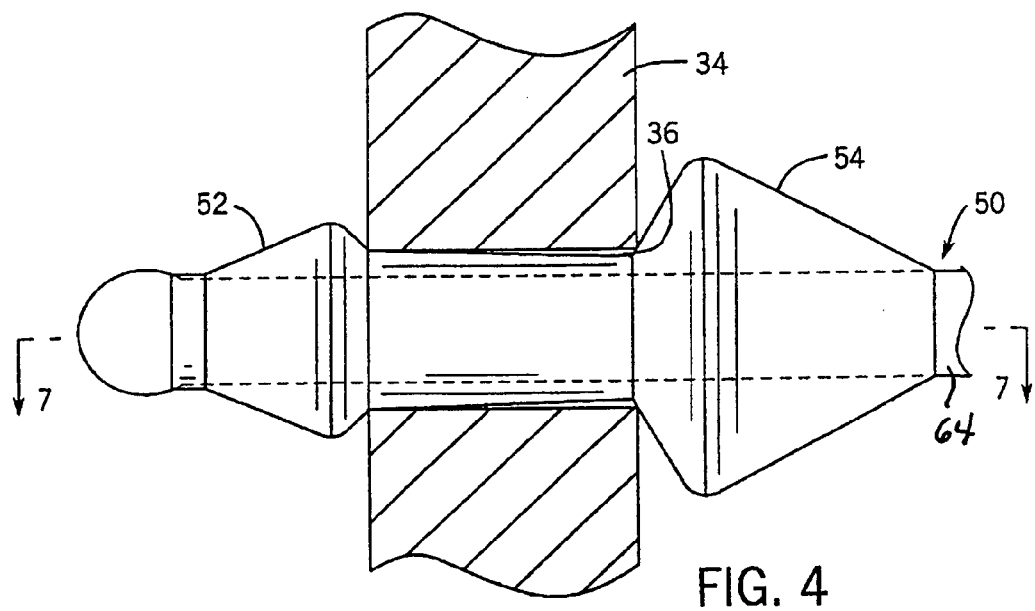
FIG. 4 illustrates a second embodiment of a return electrode in accordance with the invention, shown mounted in the modiolus.

Alternatively, as shown in FIG. 4, a second embodiment of a return electrode 50, includes resilient collars or humps 52 and 54 which, on the one hand, allow the return electrode to be inserted into a hole 36 formed in the modiolus 34 and, on the other hand, hold the return electrode 50 in place in the modiolus 34 as will be shown.

Figure 5:
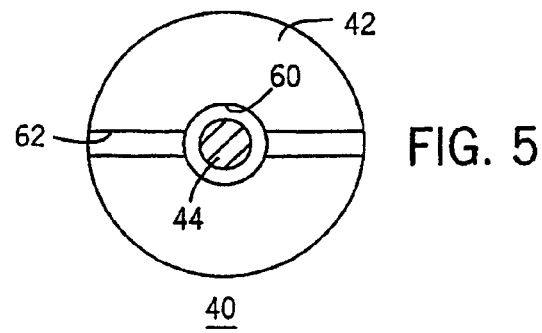
FIG. 5 is an end view of a modiolar return electrode of FIG. 3, taken in the direction of the arrows 5—5 in FIG. 3.
Figure 6:
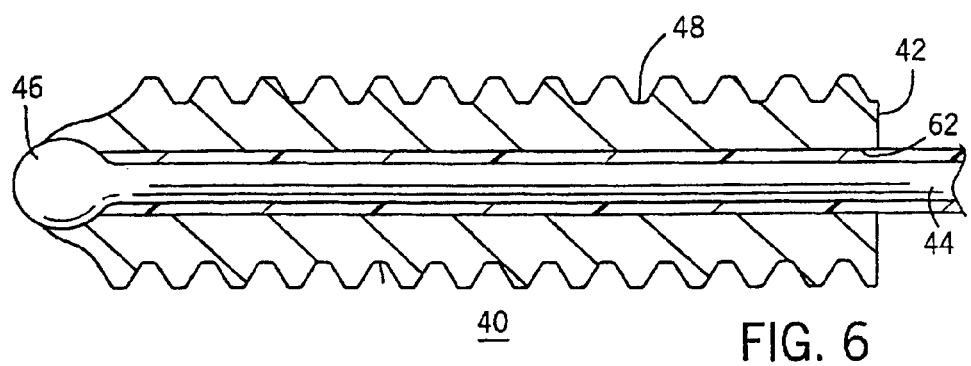
FIG. 6 is section view taken along the line 6—6 of FIG. 3.

Referring to FIGS. 3, 5, and 6, the modiolar return electrode 40 includes body portion 42 of a non-conducting metal, or alternatively Teflon and the like, and an electrode wire 44 having a tip 46 formed at its distal end. The body portion 42 has a small throughbore or tunnel 60 extending axially of the body portion 42 through which extends the electrode wire 44, as shown in FIG. 6. To form the return electrode 40, Teflon insulated platinum-iridium wire is heated until a sphere 46 forms at one end defining an exposed contact for the electrode. However, the wire is maintained insulated just to the sphere in contact 46.

In one embodiment, the electrode body portion 42 is of non-conducting metal, or alternatively Teflon and the like, and is approximately 2 mm in length and approximately 0.9 mm in diameter. The outer surface of the body portion 42 of the return electrode is threaded to allow the return electrode 40 to be screwed into the bone of the modiolus for anchoring the return electrode 40 to the modiolus. The tip of the body portion 42 of the return electrode holds the exposed contact 46 for the electrode wire 44. The other end of the body portion 42 includes a slot 62 to accommodate straight-edged screwdriver to facilitate screwing the body portion of the return electrode 40 into the hole 36 (FIG. 3) formed in the bony modiolus.

Figure 7:
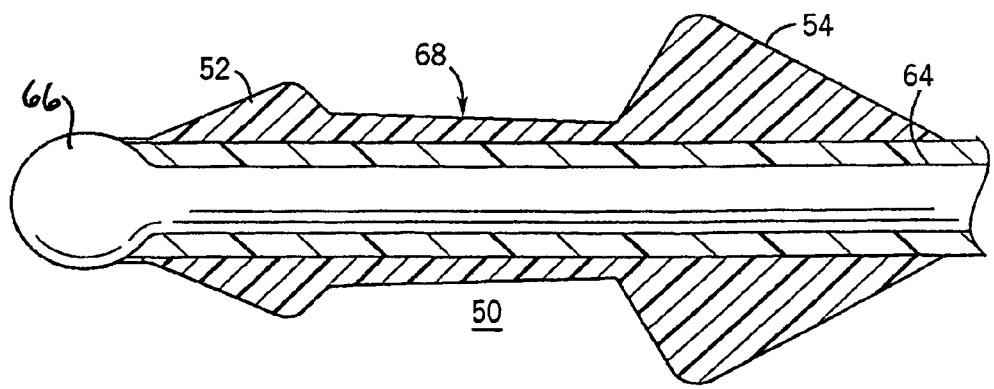
FIG. 7 is section view taken along the line 7—7 of FIG. 4.

Referring to FIGS. 4 and 7, the modiolar return electrode 50 is made of a Teflon insulated platinum-iridium wire 64, with one end fabricated into a sphere, defining an exposed contact 66. The diameter of the wire can be 120 μm and the diameter of the sphere 66 can be about 150 μm. The wire 64 is fed through an insulator 68 during implantation. The insulator 68 serves to secure the return electrode after placement into the modiolus 34 (FIG. 4) and to reseal the opening 36 drilled into the modiolus. The double hump design of the electrode 50 allows the insertion of the electrode and secures the return electrode 50 in place in the modiolus. The double hump design also provides a tight seal at the drilled hole. Ideally, the return electrode 50 becomes the core of the cochlear implant electrode and runs together with the other contact wires to an implanted processor (not shown).

To form the return electrode 50, a Teflon insulated platinum-iridium wire 64 is heated until the sphere 66 forms at the end. However, the wire is maintained insulated just to the sphere 66. The wire 64 is then placed into a model that has been filled with liquid silicone and the silicone is allowed to harden. After the silicone hardens, the model is opened and the silicone embedded wire is removed.

Referring to FIGS. 8 and 9, there is shown a further embodiment of a cochlear implant electrode array 122 in accordance with the invention. The electrode array 122 is similar to electrode array 22, but includes generally planar electrode contacts 124. Accordingly, elements of the electrode array 122 have been given the same reference numerals as like elements of electrode array 22. The electrode array 122 includes an inflatable membrane 28 of an insulating material, such as rubber, which forms the backbone of the electrode array 122. This inflatable insulator serves to increase the longitudinal resistance along the cochlear implant electrode and consequently, decreases shunting of the injected current via scala tympani. In one embodiment, the cross-sectional area of the inflatable membrane 28, when expanded, is about three to five times the cross-sectional size of the silastic carrier 31. The relatively small size of the electrode array with the inflatable membrane in an uninflated condition, facilitates placement of the electrode array into the scala tympani. Due to the increased size of the electrode array with the inflatable membrane 28 inflated, the electrode array 22 not only fills the scala tympani at the basal site of the cochlea (or the electrode), but also fills the scala tympani along the entire length of the cochlear implant electrode.

In FIG. 8, a portion of a silastic carrier 31 of the electrode array 122 is broken away to show the electrode contacts 124 of the electrode array 122. In one embodiment, the electrode array includes seventeen quadratic platinum-iridium contacts 124 which are aligned into an array. The size of each of the electrode contacts 124 can be 1×1×0.2 mm, for example. However, the electrode contacts can have other sizes and shapes, for example a spherical shape as for the contacts 24 of electrode array 22. Each of the contacts 124 is contacted by a separate Teflon insulated platinum-iridium wire 26 which can be bundled together within the silastic carrier 31 as shown in FIGS. 10 and 11. As can be seen by comparing FIGS. 10 and 11, the portion of the wire bundle nearer to the most basal electrode contacts contains more contact wires than the portion of the wire bundle at the opposite end of the electrode array. In one embodiment, the wires have a core diameter of 25 μm, and an outer diameter of 30 μm. The wires 26 are run as a bundle across the contacts 124 and are embedded in the silastic carrier 31. Moreover, the electrode contacts and the contact wires can be of other highly conductive materials. Preferably, electrical contacts and the contact wires are of the same material.

Referring also to FIGS. 10 and 11, the inflatable membrane 28 is formed over the silastic carrier 31, defining a hollow center area 37 into which extends a filling tube 35 one end of which protrudes from the basal end of the electrode array. The filling tube 35 allows connection to a syringe, or other suitable inflating mechanism, for injecting a suitable inflating material, such as silicone, into the space 37 between the silastic carrier 31 and the inflatable membrane 28 that encloses the filling tube 35. The filling tube 35 extends about two thirds the length of the body portion of the electrode array, from the most basal electrode contact to about the twelfth electrode contact 12 in a direction away for the most basal electrode contact. In one embodiment, the filling tube 35, while sealed at an inlet to the cavity 37, is not integral with the inflatable membrane 28 and/or the silastic carrier 31 for the contact wires 26. The electrode array 22 shown in FIGS. 1 and 2 can be similar to electrode array 122 as to the structure, including the inflatable membrane 28 with filling tube 35 and the silastic carrier 31 that is formed around the electrode contacts 24 and the electrode wires 26.

After the electrode array 122 (or 22) has been implanted in the cochlea through a cochleostomy into the scala tympani, the space 37 between the silastic carrier 31 and the thin membrane 28 can be filled with silicone until the thin membrane adheres to the walls of scala tympani. FIG. 10A is a section view of the electrode array illustrating the inflatable membrane 28 inflated into engagement with the scala tympani 25 shown in phantom. Because of the size and configuration of the inflatable membrane 28 of the electrode array 22, when the membrane is expanded, the electrode array not only fills scala tympani at the basal site of the cochlea (or the electrode), but also fills the scala tympani along the entire length of the cochlear implant electrode. This is very important in order to decrease the fluid space around the electrode and consequently the length constant along the scala tympani. A decreased length constant is equivalent to an increased longitudinal resistance and a decreased shunting of the current along scala tympani. To further improve the seal between the rubber membrane and the outside wall of the cochlea, the membrane 28 can be coated with growth factors. Because the membrane is coated, it will induce growth of fibrocytes which will anchor the electrode array in scala tympani 25. The filling of the backspace of the electrode array 122 (or 22) serves to reduce the free lumen of scala tympani, which results in an increased longitudinal resistance and a reduced length constant and shunting of the current via the scala tympani.

Another benefit of filling the space 37 at the backbone of the electrode array 122 (or 22) is that the implanted electrode array 122 (or 22) is urged or pushed closer to the modiolus, or into engagement with the modiolar wall, which houses the neuronal elements to be stimulated by the current injected by the electrode array. Stated in another way, in one preferred embodiment, expanding the expandable portion of the inflatable membrane 28 substantially fills the scala tympani and urges the contact electrodes into close proximity with spiral ganglion cells, or neurons in Rosenthal's canal, to allow stimulation of the neurons. For example, expanding the expandable portion of the inflatable membrane can urge the electrodes into contact with the modiolar wall (or other portion of the scala tympani) and/or provide electrical contact with nerves in the scala tympani. However, alternatively, the electrode array can be configured and arranged in other ways to bring the stimulating electrodes as close as possible to cells or neurons to be stimulated, such as through the use of any other electrical contact or conduction structure and methods that indirectly electrically couple or directly electrically connect one or more of the stimulating electrodes to cells or neurons to be stimulated.

Referring to FIG. 8, the manner in which the electrode array 122 is produced will now be described. A tapered model (not shown) is used to fabricate the insulating shell or membrane 28 that forms the body portion of the electrode array 122. In one preferred embodiment, the electrode array 122 includes flat electrode platelets or contacts 124 fabricated from platinum-iridium foil. These contacts 124 are placed on a block (not shown) such that they cover aspiration holes. During the fabrication procedure, constant suction is applied to the main canal of the mounting block to hold the electrode contacts in place. After the electrode contacts 124 have been placed, they are soldered to platinum-iridium wires 26. Next the sides of the mount block are attached and the electrode contacts 124 and the wires 26 are embedded in a silicone which forms the silastic carrier 31. The body of the electrode array 122 is kept as small as possible to allow easy and long (>20 mm) insertion of the electrode array into the cochlea. To fabricate the insulating rubber sack, a small shallow cone (the diameter of which tapers from about 2 mm to 1 mm, and about 30 mm in length) is covered with a thin rubber solution. After the rubber has dried, forming a thin membrane, the rubber sack is removed from the model and an inflating tube is glued into the open end of the rubber sack. The insulating sack and the electrode array are fused such that the rubber sack forms the backbone of the electrode array 22.

Referring again to FIG. 1, after the entire electrode array 122 (or 22) has been assembled, the electrode array is inserted into the cochlea. When the electrode array 122 (or 22) is in position in the cochlea, the space 37 that forms the rubber insulator backbone is filled with silicone, allowing the rubber membrane 28 to seal with the surrounding tissue of the cochlea and increasing the longitudinal resistance. The advantages of this electrode array 122 (and 22) over known electrode arrays are demonstrated by measurements in an artificial scala tympani and show significantly reduced power loss due to shunting currents along scala tympani, reduced current values that result in reduced risk of aberrant facial nerve stimulation and increased spatial selectivity.

The manner in which the electrode array 22 (and 122) is positioned in the cochlea and the return electrode 40 is positioned in the modiolus 34 will now be described with reference to FIGS. 12–17.

Figure 12:
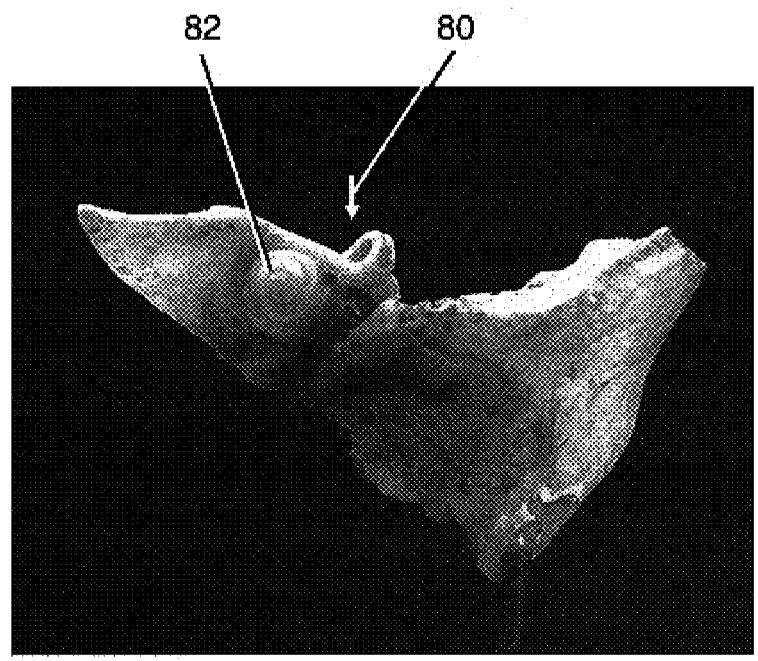
FIG. 12 is a view of a cochlea that has been drilled out from a temporal bone specimen.

In FIG. 12, the arrow 80 points to the cochlea 82 as seen drilled out from temporal bone specimen. During cochlear implant surgery, the inner ear is approached from the back to insert the stimulating electrode into scala tympani.

Figure 13:
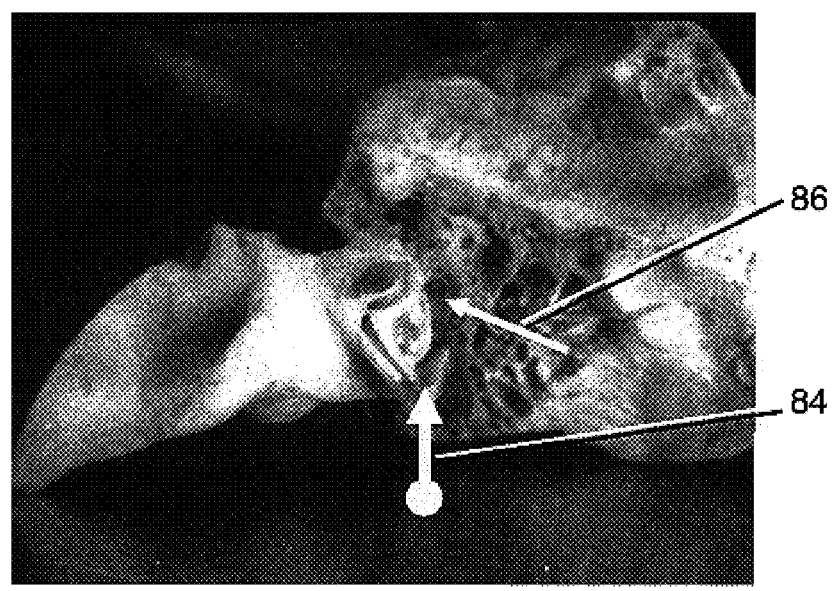
FIG. 13 is a view of drilled temporal bone as illustrating the line of sight for a surgical approach.

A curvilinear incision is made parallel to and just behind the crease of the ear. The incision is continued until the temporal bone is reached. A high-speed otologic drill is employed to remove the bone until the landmarks are available. The line of sight for the surgical approach is shown in FIG. 13 which is a view of drilled temporal bone as seen from a surgical perspective, with the arrow head 84 pointing to the incus. In FIG. 13, the long arrow 86 indicates the direction of surgical approach to the cochlea.

Referring also to FIGS. 1 and 3 the wires 26 connecting a processor to the individual electrode contacts 24 (or 124) of the electrode array 22 (or 122) run in large loops within a silicone silastic carrier 31. The Teflon insulated return electrode 40 is placed in the center of such loop, before the electrode array 22 (or 122) enters the cochlea. The return electrode 40 is separated from the silastic carrier 31 and is placed into the modiolus via the prepared hole 36 drilled into the modiolus.

Advantages of this return electrode and placement of the return electrode in accordance with the invention include nearly a threefold reduction in current amplitude needed to generate the same potential at a selected location in the modiolus and reduced current values that result in reduced risk of tissue damage and increased spatial selectivity.

Figure 14:
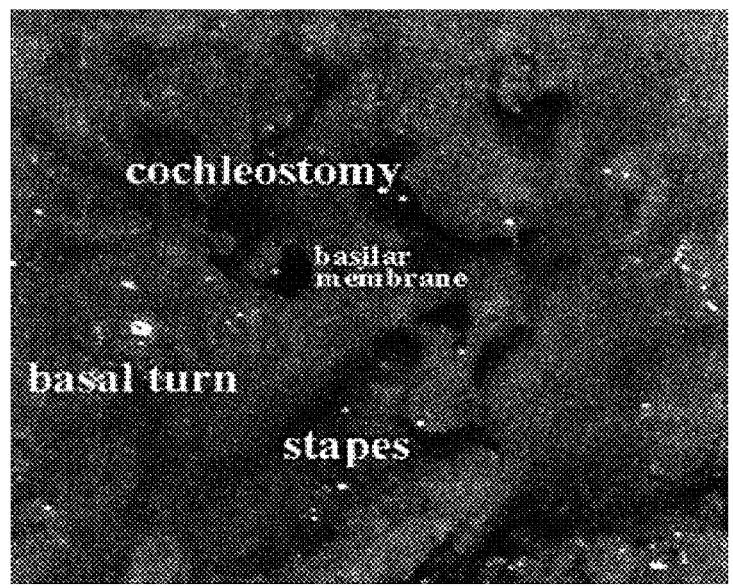
FIG. 14 is a view of cochleostomy with local landmarks labeled.

FIG. 14 shows the cochleostomy from one of the human temporal bones in the experiments. FIG. 14 is a view of cochleostomy with local landmarks labeled. A small window—facial recess—is opened in the back of the bony ear canal to gain access to the cochlea. Using a small drill, an opening, or cochleostomy, to the bony cochlea is made into the round window. The round window, which is a stable landmark on the cochlea, is one landmark for the surgeon to make the cochleostomy. In this preparation, the round window has been surgically enlarged. The location of the round window is exactly where the cochleostomy has been made.

Through the cochleostomy, the insertion of the cochlear implant is possible. After the implant is inserted, the cochleostomy is packed with locally harvested tissue to re-seal it. Incisions are closed in layers to complete the surgery. Because the membrane is coated, it will induce growth of fibrocytes which will anchor the electrode array in scala tympani. Moreover, the tissue placed at the cochleostomy also will anchor the electrode array.

Figure 15:
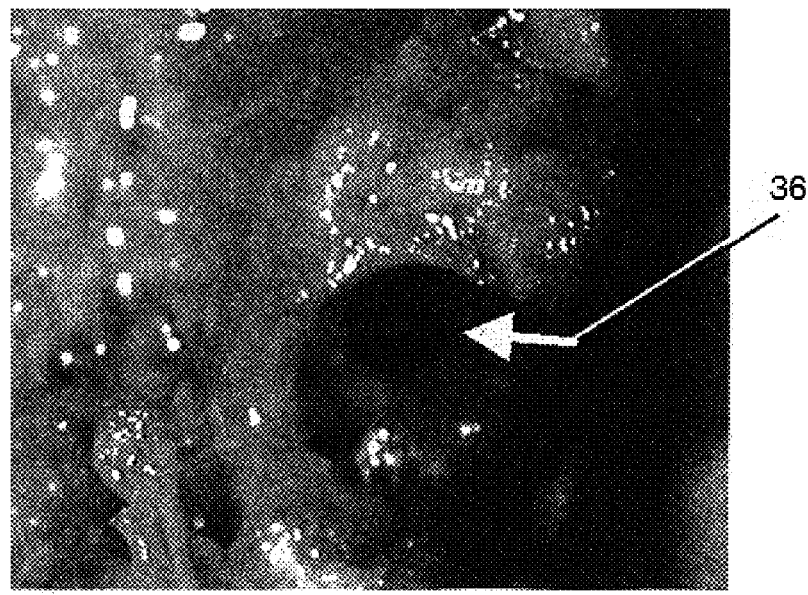
FIG. 15 is a close up view of a cochleostomy and showing the modiolar fenestration.

In accordance with the present invention, two additional steps are added to the above procedure to position the return electrode within the modiolus prior to packing the cochleostomy with tissue. Referring to FIG. 15, in the first additional step, another opening 36 is drilled deeper through the cochleostomy to reach the center of the bony cochlea. This opening 36 is termed the modiolar fenestration. FIG. 15 shows the modiolar fenestration as seen from a close-up view of the cochleostomy, with the arrow 36 pointing to the modiolar fenestration. This modiolar fenestration allows the placement of the modiolar return electrode 40 in the second additional step.

Figure 16:
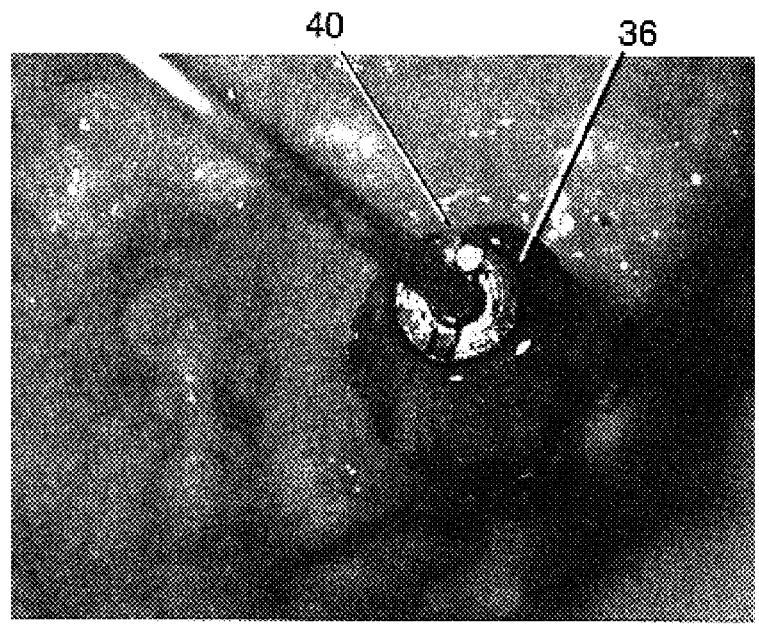
FIG. 16 is a view of the modiolar return electrode secured into the modiolar fenestration as seen from the cochleostomy.
Figure 17:
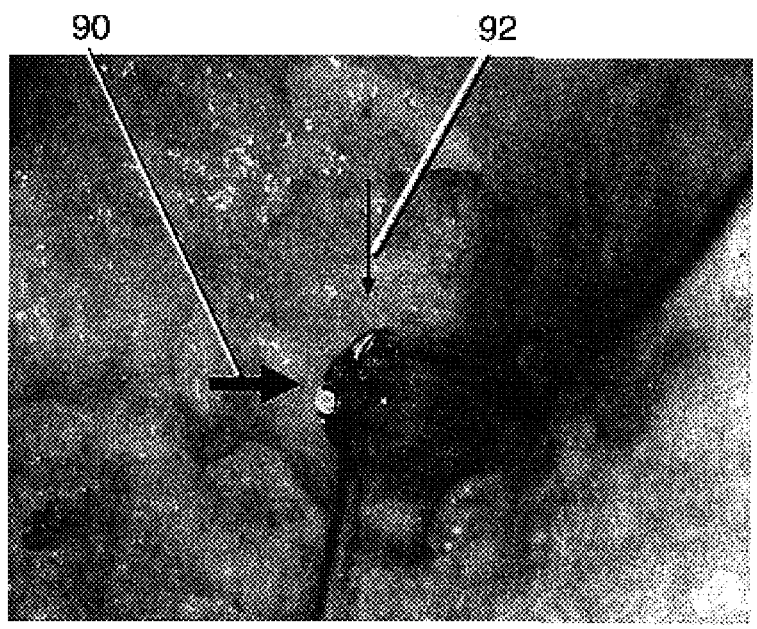
FIG. 17 is an enlarged view illustrating the modiolar return electrode and a partially inserted cochlear array accommodated in a common standard cochleostomy.

Referring to FIG. 16, the modiolar return electrode 40 is then positioned over the previously drilled modiolar fenestration 36. Using a small straight-edged screwdriver, the return electrode 40 is tightly secured into the opening or hole 36. Typically, the length of the hole is about one millimeter which allows placement and tightening of the threaded body of the return electrode 40 within the opening. The length of the hole can be determined using a probe. A return electrode of proper length, from about 0.5 mm to 1 mm, for example, is selected as a function of the length of the opening provided. The outer end of the return electrode can be flush with the surface of the modiolar wall around the opening or the tip of the electrode, at the opposite end, can protrude into the internal meatus acousticus. FIG. 16 shows the modiolar return electrode 40 secured into the modiolar fenestration 36 as viewed from the cochleostomy. After securing the modiolar return electrode, the cochlear implant 22 (or 122) can then be inserted via the cochleostomy, using known implantation techniques. FIG. 17 is an enlarged view showing that a standard cochleostomy can accommodate both the novel return electrode 40, indicated by the arrow head 90, and the partially inserted cochlear implant 22 indicated by the arrow 92.

In accordance with the present invention, the return electrode 40 is inserted into the modiolus. Overall, only two additional steps are needed surgically to implement this system. As shown in FIG. 15, modiolar fenestration 36 can be made through the standard cochleostomy. Furthermore, the electrode 40 incorporates a screw thread pattern that, when inserted, forms a tight and stable seal to the modiolar fenestration. By using a non-conducting metal, likewise Teflon, for the electrode body portion 42 (FIG. 3), the inserted electrode encourages total osseointegration that, over time, further strengthens this seal. Given that the screw-like electrode body portion does not conduct electricity, this design maintains the electrical isolation among the various compartments, vital in sustaining the proper functioning of the system.

Referring again to FIGS. 4 and 12, implantation of the return electrode 50 is performed via a post-auricular incision designed to expose the mastoid bone. This bone is then drilled and removed to provide access to the facial recess space. Opening the facial recess space allows visualization of the middle ear structures, including the crucial round window niche. An opening into the cochlea, commonly referred to as a cochleostomy is created in and around the round window (FIG. 14).

Referring to FIGS. 4 and 15, the cochleostomy not only allows clear visualization of the base of the modiolus but also permits sufficient access to drill a small hole into the area using a 0.16 mm drill bit. After the hole is drilled, the return electrode 50 can be inserted by gently pushing the tip of the electrode through the hole until the hump 52 locks into the opening. The cochlear implant electrode array 22 (or 122) is then inserted through the cochleostomy into the scala tympani. After the insertion, the cochleostomy is packed with locally harvested soft tissue to seal the opening and to provide scar formation into the region. The device is secured to the mastoid bone prior to closure of the surgical incision.

FIGS. 16 and 17 show that the modiolar return electrode 40 (or return electrode 50) can be inserted through a standard cochleostomy without significant alteration to the surgical protocol. Furthermore, the same cochleostomy can accommodate both the modiolar return electrode 40 (or 50) and a cochlear implant 40 (or 50). Overall, this concept of modiolar return electrode 40 (or 50) can be implemented with relative ease into known cochlear implants and a cochlear implant incorporating the electrode arrays 22 and 122 in accordance with the invention.

Figure 18:
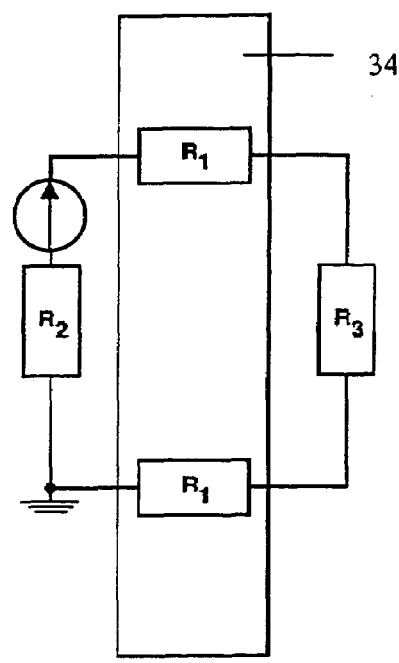
FIG. 18 is a simplified model of the electrical environment of a cochlear implant with the return electrode located outside the modiolus.
Figure 20:
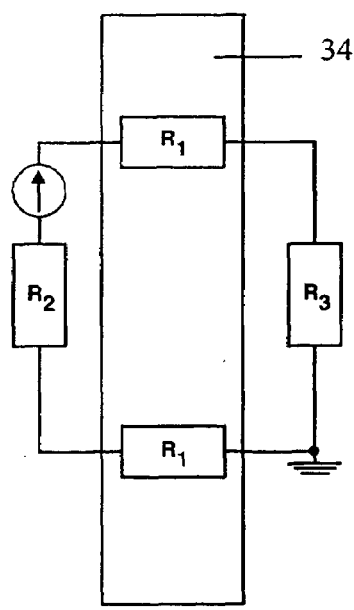
FIG. 20 is a simplified model of the electrical environment of a cochlear implant with the return electrode located inside the modiolus.
Figure 21:
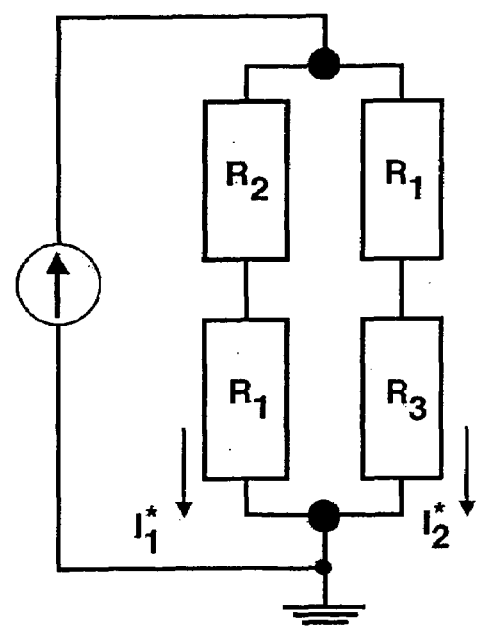
FIG. 21 represents the equivalent circuit network of FIG. 20.

Some of the benefits obtained by placing the return electrode 40 (or 50) into the modiolus are described with reference to FIGS. 18 and 20 which are simplified models of the electrical environment of a cochlear implant with the return electrode located outside of the modiolus and inside the modiolus, respectively. FIGS. 18 and 20 illustrate two possible return electrode placements. The corresponding electrical circuit diagrams are shown in FIGS. 19 and 21, respectively.

The bony wall of the modiolus 34, which separates surviving nerve fibers in the modiolus from the scala tympani, is represented by resistance $R_1$, the resistance along scala tympani by resistance $R_2$, and the resistance of the nerve tissue in the modiolus, by resistance $R_3$. All current paths are modeled with only resistive components to eliminate the frequency dependent effects.

Referring first to FIG. 18, there is shown a simplified model of the electrical environment of a cochlear implant with the return electrode located outside of the modiolus 34 and representing a modiolar wall separating the modiolus and scala tympani compartments. The resistance of the modiolar wall is represented by resistance $R_1$, the resistance along scala tympani by resistance $R_2$, and the resistance along the modiolus by resistance $R_3$. The return electrode is located outside the modiolus.

Figure 19:
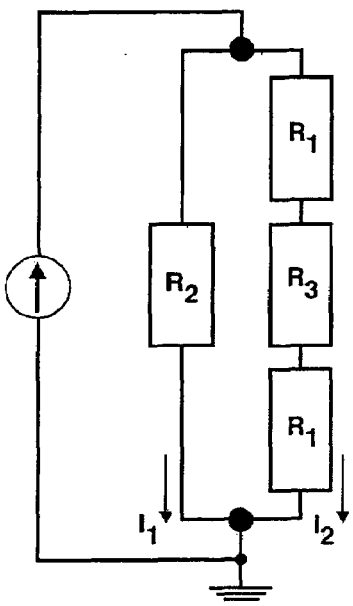
FIG. 19 represents the equivalent circuit network of FIG. 18.

FIG. 19 represents the equivalent circuit network of the model of FIG. 18 in which the return electrode is placed outside of the cochlea. Outside of the cochlea refers to any location beyond the cochlear wall. In other words, scala tympani, scala vestibuli, scala media and modiolus are considered inside. Outside the cochlea is any location beyond the cochlear wall. The current paths for an extracochlear return electrode are labeled $I_1$ and $I_2$.

Referring to FIG. 20, in the second configuration, the return electrode is placed within the modiolus. The current paths for a modiolar return electrode are labeled $I_1^*$, and $I_2^*$. FIG. 20 is a simplified model of the electrical environment of a cochlear implant with the return electrode inside the modiolus 34, representing a modiolar wall separating the modiolus and scala tympani compartments with the resistance of the modiolar wall is represented by resistance $R_1$, the resistance along scala tympani by resistance $R_2$, and the resistance along the modiolus by resistance $R_3$. and with the return electrode is located inside the modiolus. FIG. 21 represents the equivalent circuit network for the model of FIG. 20.

This simple model of the cochlea assumes that only two paths are available for the injected current in each configuration. One current path shunts flow away from the modiolus, therefore, away from the targeted structures. This path is labeled $I_1$ or $I_1^*$ in the corresponding circuit diagrams. The second path directs the current towards the modiolus, thereby, stimulating the remaining auditory neurons. This path is labeled $I_2$ or $I_2^*$ in the corresponding circuit diagrams. To determine the benefit of placing the return electrode in the modiolus, the ratio of the currents through the modiolus, $I_2^*/I_2$, is calculated.

Given the total current is the same for both return electrode placements, the following holds:

$$I = I^* = I_1 + I_2 = I_1^* + I_2^*. \tag{1}$$

For remotely placed return electrodes, the following equations can be written:

$$U = I_1(R_2) = I_2(2R_1 + R_3) = I \frac{(2R_1 + R_3)R_2}{2R_1 + R_2 + R_3} \tag{2}$$

$$\Rightarrow I_2 = I \frac{R_2}{2R_1 + R_2 + R_3}, \quad (3)$$

Similarly, for the return electrode placed into the modiolus, $I_2^*$ can be calculated:

$$U = I_1^*(R_1 + R_2) = I_2^*(R_1 + R_3) = I \frac{(R_1 + R_2)(R_1 + R_3)}{2R_1 + R_2 + R_3} \quad (4)$$

$$\Rightarrow I_2^* = I \frac{R_1 + R_2}{2R_1 + R_2 + R_3} \quad (5)$$

Consequently, the ratio $I_2^*/I_2$ of the currents is:

$$\frac{I_2^*}{I_2} = \frac{R_1 + R_2}{R_2} = 1 + \frac{R_1}{R_2}. \quad (6)$$

This ratio can be estimated by substituting resistive values for $R_1$ and $R_2$ which are known from the literature, which are available for the guinea pig: resistance $R_1$ is 2.54 k [Spelman et al., 1982], and resistance $R_2$ is 2.2 k [Johnstone et al., 1966; Cannon, 1976]. The calculated ratio is 2.1. Note that the modiolar resistance $R_3$ does not appear in the current ratio expression given by equation (6). This fact implies that changes in resistance within the confines of the modiolus during experimentation should not alter the current ratio. However, the modiolar resistance between the two measuring electrodes can be estimated from values published by von Békésy [von Békésy, 1951]. He obtained 10 k for the resistance of the entire modiolus. The length of the guinea pig modiolus is approximately 4 mm, and consequently the value of resistance $R_3$ is 2.5 k. Knowing the values for all three resistances $R_1$, $R_2$ $R_3$ of the model allows the current distribution to be calculated:

$$I_1 R_2 = I_2(2R_1 + R_3), \text{ and} \quad (7)$$

$$\frac{I_1}{I_2} = \frac{2R_2 + R_3}{R_2} \cong 3. \quad (8)$$

Consequently, 75% of the current injected into the parallel circuit with the return electrode located outside the modiolus is shunted away from the modiolus. This prediction is in close agreement with the experimental value reported in the literature. For example, Spelman et al. (1982) found that approximately 75% of the current injected into the scala tympani was shunted away from the modiolus when the return electrode was located outside the modiolus.

Experimental results from the four human temporal bone preparations yielded an average ratio of 2.4 which is in close agreement with the model's prediction. Consequently, to achieve an equivalent modiolar current, the total current produced by the active electrode can be reduced by more than half if the return electrode is moved to the modiolus. In turn, the power required to produce effective stimulation can be reduced drastically.

The power W is calculated by $$W = I^2 * R, \quad (9)$$

where I denotes the total current and R the total resistance of the network. With the return electrode in the modiolus, the total current can be reduced by 2.4 times to achieve the same modiolar currents as for a return electrode that is located outside of the modiolus. In other words, the power between the two return electrode placements (inside and outside the modiolus) will be compared for the same modiolar current, $I_2 = I_2^*$. Consequently, $I^* = I/2.4$. The power ratio between the two configurations then is calculated as follows:

$$\frac{W^*}{W} = \frac{(I^*)^2 R^*}{(I)^2 R} = \frac{(I^*)^2}{(I)^2} \frac{(R_1 + R_2)(R_1 + R_3)}{(2R_1 + R_3)R_2}. \quad (10)$$

With a current ratio of 2.4, the corresponding power ratio becomes $$\frac{W^*}{W} = \frac{(I)^2 R^*}{2.4^2 (I)^2 R} \frac{(R_1 + R_2)(R_1 + R_3)}{2.4^2 (2R_1 + R_3)R_2}. \quad (11)$$

This ratio can be estimated by substituting resistive values for $R_1$, $R_2$ and $R_3$ from the literature, which are available for the guinea pig: $R_1$ is 2.54 k [Spelman et al., 1982], and $R_2$ is 2.2 k [Johnstone et al., 1966], and $R_3$ is 2.5 k [von Békésy, 1951]. The ratio would be approximately 1:4.

Experiments

Experiments demonstrating the effects of return electrode placement were performed on four preserved human temporal bones. The experiment is designed to measure current flow within the modiolus by placing a stimulating electrode into scala tympani, and a return electrode within the modiolus and at several locations outside of the cochlea. Special measuring electrodes were fabricated to permit current measurements within the modiolus.

Preparation of temporal bones for measurements: Four human temporal bones were prepared using the following procedures. First, the basal turn of the cochlea and the round window niche were clearly identified for orientation. Following published surgical procedures, a cochleostomy was created near the round window niche to permit insertion of a stimulating electrode into scala tympani. Next, the internal auditory canal was enlarged circumferentially without violating the labyrinth. The cochlear nerve then was identified and dissected laterally towards the modiolus. Care was taken not to drill into the basal turn of the cochlea. The internal auditory canal and modiolus were opened sufficiently to allow insertion of the measuring electrodes. The specimen then was reduced to a small block containing only the petrous portion of the temporal bone, measuring approximately 5×5×5 cm. The smaller specimen permitted flexible handling and positioning during the experiments. The blocks were stored in the Hank's balanced Salt Solution (HBSS) for at least three days prior to any measurements.

Mounting of the temporal bone for measurements: During the experiments, the temporal bone block was secured in a Petri dish. The bone was fixed in place using a 2.5% agar gel in Hank's solution, made by dissolving 2.5 grams of agar powder in 100 ml of HBSS. First, the block was positioned in the Petri dish to allow insertion of the stimulating electrode via the cochleostomy and placement of the recording electrode into the modiolus. Then, the agar solution was poured into the dish and allowed to harden with the temporal bone block held in this position. Next, a Teflon-insulated silver wire electrode (diameter 250 μm total, 200 μm core)

was inserted 10 mm into scala tympani, simulating an active electrode of a cochlear implant. The silver wire electrode permitted precise placement of the current source in each temporal-bone specimen. The measuring electrode was mounted to a micro-manipulator and lowered into the center of the modiolus just prior to measurement.

Measurements

Figure 22:
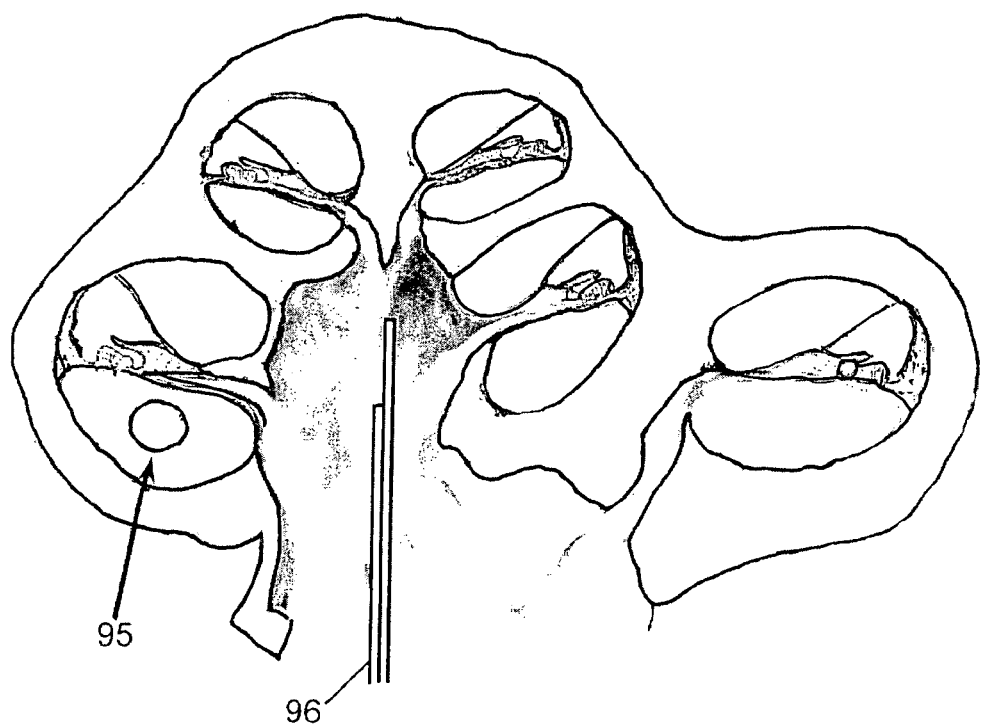
FIG. 22 shows a human temporal bone experimental setup, a cross-sectional view of cochlea with a silver wire electrode located in the scala tympani and with a measuring-electrode pair in the opened modiolus.

Referring to FIG. 22, there is shown a human temporal bone experimental setup, a cross-sectional view of cochlea is seen with a silver wire stimulating electrode 95 in the scala tympani and the measuring-electrode pair 96 in the opened modiolus. The measuring electrodes consist of two intertwined wires separated by 1 mm at the tips.

The measuring electrodes 96 included two intertwined Teflon-insulated silver wires (diameter 125 µm total, 75 µm core) separated vertically by 1 mm (FIG. 22). The wires were held by a fine glass-pipette and mounted to the micro-manipulator. The entire assembly was lowered into the modiolus parallel to its longitudinal axis, as shown in FIG. 22. The electrodes were connected to a high-impedance differential amplifier (impedance>$10^{11}$, ISO-80, WPI, Sarasota, Fla.) to measure the voltages between the two electrodes. Voltages could not be directly converted into currents, because the resistance along the modiolus, resistance $R_3$ (FIG. 20), was unknown. However, the resistance between the contacts of the measuring electrodes remained the same for both measuring configurations. Therefore, the ratio between the obtained voltages with the return electrode located in the modiolus and with those located outside the modiolus equaled the respective current ratio. As discussed with the model, this ratio reflects the advantage of placing the return electrode in the modiolus.

Voltage measurements were made for several return-electrode placements: outside the cochlea in various regions of the agar gel, in the round window niche, and in the modiolus. In this study, only AC currents (10 Hz) of different amplitudes (10 to 500 µA) were applied using a current calibrator (Model 2500, Valhalla Scientific, San Diego, Calif.). The current calibrator was controlled by a waveform-generator (HP 33120A, Hewlett Packard, Loveland, Colo.). At 10 Hz, no detectable frequency shifts between stimulus and response waveforms were detected on the oscilloscope. Current amplitudes were adjusted as needed until response waveforms were stable and reproducible. A paired t-test was performed to determine statistical significance between the measured voltages with return electrode located in the modiolus and in the extra-cochlear locations.

Control measurements: In order to verify the reproducibility of the measurements the measurements were repeated five times in one temporal bone. For these measurements, the stimulating electrode was in the scala tympani, the return electrode in agar gel, and the measuring electrode in the modiolus. The five measurements yielded similar voltage readings of 105±3 mV (temporal bone specimen 4). Subsequent temporal bone experiments consisted of one modiolar voltage measurement for each return electrode locations.

TABLE I

Measured voltages in human temporal bone specimen 1

| Ground electrode locations | Measured Voltage |
|---|---|
| Modiolus | 144 mV |
| Round window niche | 62 mV |
| Agar gel | |

TABLE I-continued

Measured voltages in human temporal bone specimen 1

| Ground electrode locations | Measured Voltage |
|---|---|
| Superior | 64 mV |
| Inferior | 64 mV |
| Anterior | 64 mV |
| Posterior | 64 mV |

Agar gel locations describe relative anatomic locations of the return electrode to the cochlea. For instance, "Superior" indicates that the return electrode is placed in an anatomically superior location relative to the cochlea.

Measurements with the return electrode outside the cochlea: Measurements obtained from temporal bone specimen 1 are shown in Table I. Voltage values were similar for all return electrode locations outside the modiolus, including various locations in the agar and in the round window niche. Because of this finding, the "outside modiolus" category broadly encompasses all locations of return electrode outside the modiolus. In subsequent experiments, "outside modiolus" measurements were performed with the return electrode in the agar, anatomically posterior to the cochlea.

TABLE II

Measured voltages in human temporal bone
Voltage obtained with ground electrode

| Outside Modiolus (Ro) | Inside Modiolus (Ri) | Ratio (Ri/Ro) |
|---|---|---|
| Temporal bone #1 64 mV | 144 mV | 2.3 |
| Temporal bone #2 59 mV | 161 mV | 2.7 |
| Temporal bone #3 92 mV | 263 mV | 2.9 |
| Temporal bone #4 105 mV | 188 mV | 1.8 |
| Mean ± SD 80 mV ± 22 | 189 mV ± 52 | 2.4 |

Measurements with the return electrode in the modiolus: Combined results from the four human temporal bones are shown in Table II. For each temporal bone specimen, measured potentials are significantly higher with the return electrode located inside the modiolus compared to the extracochlear location in the agar. A paired t-test showed that the potential differences were statistically significant ($p<0.01$). The voltage ratio between the two different return electrode locations was computed. The average ratio was 2.4±0.5, ranging from 1.8 to 2.9.

The simple model predicted that return electrode placement in the modiolus would provide 2.7 times higher modiolar currents compared with remotely located return electrodes. This ratio was derived using resistance values reported for the guinea pig cochlea. Our experimental results from the four human temporal bone preparations yielded an average ratio of 2.4, which is in close agreement with the model's prediction. This concordance suggests that the simple model may provide some insight into the current behaviors within the cochlea.

These results clearly demonstrate that placing a cochlear-implant return electrode inside the modiolus can improve operating efficiency. Presently, a large fraction of current produced by a cochlear implant does not enter the modiolus, but instead is shunted via less resistive paths within the cochlea as is known. Only currents entering the modiolus are capable of stimulating the auditory nerve, thereby facilitating auditory perception. Return electrodes located in the modiolus direct the stimulating currents into the modiolus and thereby reduce the degree of shunting within the cochlea. Modiolar currents achieved with this configuration are more than two times greater compared to a remotely located return electrode. Consequently, to achieve the same modiolar current, the total current produced by the active electrode can be reduced by more than half. In turn, the power required to produce effective stimulation can be reduced.

Similarly, the increase in modiolar current indicates concomitant reduction in the current shunted through scala tympani or other extracochlear paths. This reduction may lead to another advantage of proposed configuration, namely to decrease the incidence of aberrant facial nerve stimulations. More than 7% of the implanted patients complain of this stimulation, especially those with otosclerosis. The aberrant stimulation usually results from active electrodes located in the basal turn of the cochlea, adjacent to the labyrinthine segment of facial nerve. Although the precise mechanism of facial nerve stimulation is debated, an injected current probably spreads into this region and can lead to activation of the facial nerve. Thus, decreasing the current necessary to stimulate auditory nerve fibers may reduce the risk of this side effect.

Further testing has demonstrated that placing the return electrode in the modiolus can increase modiolar current amplitudes. The current required to elicit a compound action potential via a scala tympani electrode can be reduced if the return electrode is moved from a remote location to the modiolus. Concomitant with the decrease in current amplitude, an increase in spatial selectivity of the cochlear implant electrode can be obtained.

More specifically, the hypothesis that a modiolar return electrode increases the current through the modiolus and reduces the current necessary for an auditory response was tested in the present experiments. Electrically evoked brainstem potentials were recorded for different placements of the return electrode. Initial measurements of acoustically evoked auditory brainstem responses provided a gross measure of cochlear function. After placing a stimulation electrode into the first turn of a gerbil cochlea, current amplitudes to elicit electrically evoked brainstem potentials were determined for various placements of the return electrode. Return electrode placements included the jaw, the bulla close to the apex of the cochlea, scala tympani and the modiolus.

Animal surgery was performed as described previously (in Emadi and Richter, 2002). In short, the gerbils were anesthetized by an initial intraperitoneal injection of sodium pentobarbital (80 mg/kg body weight). Maintenance doses were 17 mg/kg bodyweight and were given throughout an experiment, whenever the animal showed signs of increasing arousal, assessed every thirty minutes by a paw withdrawal reflex. After the animal was fully anesthetized, breathing was facilitated by performing a tracheotomy and securing a length of PE90 tubing into the opening in the trachea. The animal then was positioned, belly down, on a heating pad used to maintain body temperature at 38° C., and its head was stabilized in a heated head holder. Two chest electrodes were attached to monitor heart rate.

An opening (0.2 mm) was created in scala tympani in the basal turn of the cochlea. A pair of silver wires (diameter 125 μm total, 75 μm core) separated 0.5 mm apart were inserted into scala tympani through this opening. Furthermore, electrodes were placed in the neck muscle and on the apex of the cochlea.

Cochlear function was determined using auditory brainstem responses (ABRs). Acoustic stimuli (clicks) were generated by a 0.1 ms electrical sinusoidal voltage command (one cycle of a 10 kHz tone) presented at a rate of 5 Hz to a Beyer DT 770Pro headphone. The speculum of the speaker was placed directly in front of the ear canal (quasi free field). Differential responses from intradermal electrodes were obtained by subtracting ispislateral mastoid from vertex potentials measured relative to a ground electrode placed in the neck. The electrodes were connected to a differential amplifier (ISO-80, WPI, Sarasota, Fla.) set at 10,000 times amplification. Further amplification and filtering (300 to 3000 Hz) of the signal was obtained through a filter (Frequency Devices, IP90). The sampling rate was 200,000, and the results of 200 trials were averaged.

In addition to acoustic stimulation, auditory brainstem responses were also evoked by electric currents. In particular, the current amplitude were determined to evoke a neuronal response. Measurements were made while one electrode was placed in scala tympani and a second electrode was placed either in the jaw, scala tympani, or the base of the modiolus.

Electric stimuli consisted of charge balanced biphasic pulses (0.5 ms each phase). The pulses were generated using custom written software and a Digital-to-Analog computer board (KPCI-3116, Keithley) and were used to control an AC/DC current calibrator (Model 2500, Valhalla Scientific, San Diego, Calif.). The stimulating electrodes were directly connected to the current calibrator. Current amplitudes of 100 μA were applied and were decreased sequentially by 10 μA until the threshold level was obtained or a current amplitude of 1 μA was reached.

Again, differential responses from intradermal electrodes were obtained by subtracting ipsilateral mastoid from vertex potentials measured relative to a ground electrode placed in the neck. In contrast to acoustic stimulation, for electrical stimulation the electrodes were connected to a differential amplifier (ISO-80, WPI, Sarasota, Fla.) set at 100 times amplification. Further amplification (1000 times) and filtering (1 Hz to 50,000 Hz) of the signal was obtained through a filter (Frequency Devices, IP90). The total amplification was 100 dB. Sampling rate was 200,000 with 1024 averages being performed at each current level.

The experiment were terminated by a lethal injecting of sodium-pentobarbital. To demonstrate the absence of auditory brainstem responses, thirty minutes after death, click-evoked ABRs and electrically evoked ABRs using the scala tympani electrodes were repeated.

The results show that current amplitudes were significantly smaller when the return electrode was placed in the modiolus as illustrated in Table III. While the ratio of the currents to reach threshold was about three when the modiolar return electrode placement was compared to scala tympani placements, the ratio was about 2.3 for the return electrode in the modiolus versus the electrode in the jaw. A return electrode placed in the jaw and in scala tympani would correspond to typical placements of the return electrode in contemporary cochlear implants.

TABLE III

Current necessary to elicit an electrically evoked auditory brainstem response for the return electrode.

| (a) Jaw µA | (b) Apex µA | (c) Bipolar µA | (d) Modiolus µA | (e) Ratio Jaw/Modiolus | (f) Ratio Bipolar/Modiolus |
|---|---|---|---|---|---|
|  |  | 70 |  |  |  |
| 35 | 35 | 75 |  |  |  |
| 55 | 45 | 75 |  |  |  |
| 35 |  | 55 | 15 | 2.3 | 3.7 |
|  |  | 55 |  |  |  |
| 55 |  | 75 | 25 | 2.2 | 3 |
|  |  | 55 | 25 |  | 2.2 |
| 95 |  | 125 | 35 | 2.7 | 3.6 |
| 50 | 40 | 73 | 25 | 2.1 | 2.5 |

Table III shows the current necessary to elicit an electrically evoked auditory brainstem response for the return electrode in the jaw (column a), at the apex of the cochlea (column b), in scala tympani (column c), and in the modiolus (fourth column). Columns e and f give the ratios for the different return electrode placements. Each row represents the results obtained for one animal.

Although exemplary embodiments of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A method of positioning a cochlear implant in a human cochlea that includes a modiolus having a modiolar wall adjacent to scala tympani of the cochlea, the cochlear implant including a stimulating electrode array and a return electrode, wherein the stimulating electrode array includes a flexible insulating member, a plurality of electrode contacts disposed on one side of the flexible insulating member in a spaced relation, and a plurality of electrode wires extending within the flexible insulating member, said method comprising the steps of:
   locating the return electrode within the cochlea with at least a portion of the return electrode positioned adjacent to the modiolus;
   anchoring the return electrode to the modiolar wall;
   providing an expandable portion along a second side of the flexible insulating member;
   inserting the electrode array into the scala tympani with the expandable portion in an unexpanded form; and
   expanding the expandable portion of the insulating member to substantially fill the scala tympani and to urge the electrode contacts into close proximity with neurons in Rosenthal's canal.

2. The method according to claim 1, wherein the step of anchoring the return electrode to the modiolar wall includes the steps of providing an opening in the modiolar wall, and locating at least a portion of the return electrode within the opening in the modiolar wall.

3. The method according to claim 2, wherein the step of anchoring the return electrode to the modiolar wall includes the step of securing said portion of the return electrode within the opening in the modiolar wall.

4. The method according to claim 3, wherein the step of securing the return electrode in the opening in the modiolar wall includes the step of providing a threaded engagement between said portion of the return electrode and an inner surface of the opening in the modiolar wall.

5. The method according to claim 3, wherein the step of securing the return electrode in the opening in the modiolar wall includes the steps of providing at least one projection on the return electrode, and positioning the return electrode in the opening with said projection in engagement with a surface of the modiolar wall.

6. The method according to claim 1, including locating the return electrode within the cochlea, allowing the return electrode to be inserted into the scala tympani along with the electrode array for anchoring to the modiolar wall.

7. A method of positioning a cochlear implant in a human cochlea that includes a modiolus having a modiolar wall adjacent to scala tympani of the cochlea, the cochlear implant including a stimulating electrode array and a return electrode, the stimulating electrode array including a flexible insulating member, a plurality of electrode contacts disposed on one side of the flexible insulating member in a spaced relation, and a plurality of electrode wires extending within the flexible insulating member, said method comprising the steps of:
   locating the return electrode within the cochlea with at least a portion of the return electrode adjacent to the modiolus;
   anchoring the return electrode to the modiolar wall;
   providing an expandable portion along a second side of the flexible insulating member;
   inserting the electrode array into the scala tympani with the expandable portion in an unexpanded form; and
   expanding the expandable portion of the insulating member to urge the electrode contacts into close proximity with or contact with neurons in Rosenthal's canal.

8. The method according to claim 7, wherein the step of anchoring the return electrode to the modiolar wall includes the steps of providing an opening in the modiolar wall, and locating at least a portion of the return electrode within the opening in the modiolar wall.

9. The method according to claim 8, wherein the step of anchoring the return electrode to the modiolar wall further includes the step of securing said portion of the return electrode within the opening in the modiolar wall.

10. The method according to claim 9, wherein the step of securing the return electrode in the opening in the modiolar wall includes the step of providing a threaded engagement between said portion of the return electrode and an inner surface of the opening in the modiolar wall.

11. The method according to claim 9, wherein the step of securing the return electrode in the opening in the modiolar wall includes the steps of providing at least one projection on the return electrode, and positioning the return electrode in the opening with said projection in engagement with a surface of the modiolar wall.

12. A method of locating a return electrode of a cochlear implant in a human cochlea that includes a modiolus having a modiolar wall, said method comprising the steps of:
   providing an access to the modiolar wall through at least one access opening;
   providing an opening through the modiolar wall to expose tissue;
   inserting the return electrode into said opening in the modiolar wall;
   positioning the return electrode within said opening in the modiolar wall; and securing the return electrode within said opening in the modiolar wall.

13. The method according to claim 12, wherein the step of positioning the return electrode within said opening in the modiolar wall includes the step of locating a contact portion of the return electrode in contact with said exposed tissue.

14. The method according to claim 12, wherein the step of positioning the return electrode within said opening in the modiolar wall includes the step of locating the return electrode to have first and second ends located at opposite sides of the modiolar wall.

15. The method according to claim 12, wherein the step of securing the return electrode includes the step of providing a threaded engagement between a portion of the return electrode and an inner surface of the opening in the modiolar wall.

16. The method according to claim 12, wherein the step of securing the electrode includes the steps of providing at least one projection on the return electrode, and positioning the return electrode in the opening with said projection in engagement with a surface of the modiolar wall.

17. The method according to claim 12, wherein the step of securing the electrode includes the steps of providing at least one projection and one stop surface on the electrode and engaging said one projection and said stop surface with surfaces of the modiolar wall to secure the return electrode to the modiolar wall.

18. A method of locating a single return electrode of a cochlear stimulating electrode array in a human cochlea that includes a modiolus having a modiolar wall, said method comprising the steps of:
providing an access opening to the modiolar wall;
inserting the return electrode through the access opening to be located adjacent to the modiolar wall; and
securing the return electrode to the modiolar wall.

19. A method of improving response of a cochlear implant located in scala tympani of a human cochlea, the cochlea including a modiolus having a modiolar wall adjacent to the scala tympani, wherein the cochlear implant includes a stimulating electrode array including a flexible insulating member, a plurality of electrode contacts disposed on one side of the flexible insulating member in a spaced relation, and a plurality of electrode wires extending within the flexible insulating member, said method comprising the steps of:
providing an opening in the modiolar wall;
positioning at least a portion of a return electrode in said opening in the modiolar wall;
securing the return electrode to the modiolar wall;
inserting the electrode array into the scala tympani; and
causing the electrode contacts of the stimulating electrode array to be urged into close proximity with neurons in Rosenthal's canal.

20. The method according to claim 19, wherein the step of causing the electrode contacts of the stimulating electrode array to be urged into close proximity with neurons in Rosenthal's canal includes the steps of providing an expandable portion along a second side of the flexible insulating member; inserting the electrode array into the scala tympani with the expandable portion in an unexpanded form; and expanding the expandable portion of the insulating member.

21. A cochlear implant adapted to be implanted in scala tympani of a human cochlea, the cochlea including a modiolus having a modiolar wall adjacent to the scala tympani, said cochlear implant comprising:
a stimulating electrode array including a plurality of electrode contacts, a plurality of conductors electrically connected to the electrode contacts, a flexible insulating member containing the conductors, the flexible insulating member including an expandable portion adapted to be expanded to substantially fill the scala tympani; and
a return electrode adapted for mounting within the cochlea with at least a portion of the return electrode extending into the modiolar wall.

22. The cochlear implant according to claim 21, wherein the return electrode is adapted to be received within an opening in the modiolar wall.

23. A return electrode for a cochlear implant that is adapted to be located in scala tympani of a human cochlea, the cochlea including a modiolus having a modiolar wall with an opening formed in the modiolar wall, said return electrode comprising:
a body of an electrically insulating material adapted for insertion into the opening in the modiolar wall;
an electrode including a conductor having a contact at one end, the conductor extending through the body; and
the body defining a retaining mechanism for securing the body to the modiolar wall.

24. The return electrode according to claim 23, wherein the conductor is a single wire.

25. The return electrode according to claim 23, wherein the body has a threaded outer surface defining the retaining mechanism.

26. The return electrode according to claim 23, wherein the body has a slot to facilitate positioning of the electrode within the opening.

27. The return electrode according to claim 23, wherein the body has an axial bore and the conductor extends through the axial bore.

28. The return electrode according to claim 23, wherein the body has a threaded outer surface defining the retaining mechanism, allowing the body to be received in threaded engagement with the opening in the modiolar wall.

29. The return electrode according to claim 23, wherein the electrode has a tip portion that is generally spherical in shape.

30. A return electrode for a cochlear implant that is locatable in scala tympani of a human cochlea, the cochlea including a modiolus having a modiolar wall adjacent to the scala tympani, said return electrode comprising:
a body of a flexible material;
an electrode including a conductor having a contact at one end, the electrode molded into the flexible material; and
the body having at least one projection for securing the body to the modiolar wall.

31. The return electrode according to claim 30, wherein the conductor is a single wire.

32. The return electrode according to claim 30, wherein the projection projects from the body near a first end thereof, and including a second projection spaced apart axially from the first projection, at least one of the first and second projections being resilient to allow said one projection to deflect during insertion of the electrode into the opening in the modiolar wall.

33. The return electrode according to claim 31, wherein the wire includes a tip and insulation that extends up to the tip.

34. The return electrode according to claim 33, wherein the tip of the wire is generally spherical in shape.

* * * * *